United States Patent [19] [11] Patent Number: 5,314,695
Brown [45] Date of Patent: May 24, 1994

[54] TISSUE FACTOR BASED PROTHROMBIN TIME REAGENT

[75] Inventor: Scott M. Brown, San Diego, Calif.

[73] Assignee: Corvas International, Inc., San Diego, Calif.

[21] Appl. No.: 784,326

[22] Filed: Oct. 29, 1991

Related U.S. Application Data

[63] Continuation-in-part of Ser. No. 612,118, Nov. 13, 1990, abandoned.

[51] Int. Cl.$^5$ ............................................. A61K 9/127
[52] U.S. Cl. ............................... 424/450; 428/402.2; 436/69; 514/21
[58] Field of Search ............... 424/450; 428/402.2; 264/4.1, 4.3, 4.6; 514/2, 21; 530/381; 436/18, 69

[56] References Cited

U.S. PATENT DOCUMENTS

| | | | |
|---|---|---|---|
| 3,179,567 | 4/1965 | Owren | 530/381 |
| 4,595,680 | 6/1986 | della Valle | 514/77 |
| 4,857,319 | 8/1989 | Crowe | 424/450 X |
| 5,017,556 | 5/1991 | O'Brien | 530/380 |

OTHER PUBLICATIONS

Wijngaards BBA 488, 161, 1977.

Primary Examiner—Thurman K. Page
Assistant Examiner—G. S. Kishore
Attorney, Agent, or Firm—Lyon & Lyon

[57] ABSTRACT

Prothrombin time reagents are provided which comprise novel liposome compositions in which tissue factor is associated with an inserted into the phospholipid bilayer of the liposomes. Methods for their preparation are also provided. The liposome compositions may be adjusted to allow maximum coagulant activity and sensitivity to extrinsic coagulation factors.

9 Claims, 2 Drawing Sheets

TISSUE FACTOR BASED PROTHROMBIN TIME REAGENT

CROSS REFERENCE TO RELATED APPLICATIONS

This application is a continuation-in-part of the commonly assigned patent application U.S. Ser. No. 07/612,118 for "Tissue Factor Based Prothrombin Time Reagent", filed Nov. 13, 1990 abandoned, the disclosure of which is incorporated herein by reference.

BACKGROUND OF THE INVENTION

1. Field of the Invention

The present invention relates to a prothrombin time (PT) reagent using purified, reconstituted natural or recombinant human tissue factor (rTF). More particularly, the invention relates to the reconstitution of tissue factor (TF) into phospholipid vesicles or micelles to produce a tissue factor-based PT reagent. Such a reagent allows specific monitoring of oral anticoagulant therapy and deficiencies in the extrinsic pathway of coagulation.

2. Description of Related Art and Introduction to the Invention

In general, liposomes are a general category of vesicle which comprise one or more lipid bilayers surrounding an aqueous space. Within this category are unilamellar vesicles composed of a single membrane or lipid bilayer, and multilamellar vesicles composed of many concentric membranes (or lipid bilayers). Liposomes are commonly prepared from phospholipids. Szoka, F. and Papahadjopoulos, D., Ann. Rev. Biophys. Bioeng., 9:467–508 (1980). Micelles are different from liposomes. Micelles form when molecules possessing both hydrophobic and hydrophilic properties, such as detergents, are put into aqueous media. The hydrophobic portions of the molecules aggregate to avoid the aqueous media. In their simplest state, micelles may be spherical; however, they may form aggregates (bilayers) of various shapes and sizes. Micelles differ from liposomes in having a hydrophobic interior rather than an aqueous interior. For example, the hydrophilic heads of the detergent molecules comprising the micelle face outward into the water while the hydrophobic tails join company with other like hydrophobic structures. Davis, B. D. and Dulbecco, R. "Sterilization and Disinfection." Microbiology, 3rd Edition, p 1270, Harper & Row (Davis, B. D., et al., 1980); Mahler, H. R. and Cordes, E. H., Biological Chemistry, Second Edition, Harper & Row Publishers, pp. 712–714 (1971).

Liposomes have been used as a drug delivery system. This approach takes advantage of the fact that liposomes have a relatively impervious lipid bilayer which may enclose an interior aqueous space and thereby provide a method to completely encapsulate various drugs within this interior space. Szoka, supra, at p. 468. An important aspect of a delivery system of this type would be that the active ingredient drug was unavailable to the aqueous medium outside the liposome until it reached its target. Janoff et al., U.S. Pat. Ser. No. 4,880,635 (1989).

It has been observed that the tissues of vertebrates, when added to citrated plasma and recalcified, will profoundly accelerate clotting time. This tissue constituent which has been observed to activate the coagulation protease cascades is commonly referred to as thromboplastin or tissue factor (TF).

In 1935, the use of thromboplastin (procoagulant tissue factor) was first described in a one stage PT test (Quick, J. Biol. Chem., 109:73–74, 1935). This test employed thromboplastin derived from mammalian tissue and a standard curve prepared with dilutions of pooled normal human plasma. The modern version of this test is easy to perform and can be automated.

The prothrombin time (PT) test is the most commonly performed assay in the coagulation laboratory. Variants of this test have a number of uses (White, et al., Hemostasis and Thrombosis, Basic Principles and Clinical Practice, Coleman, et al., eds., J. B. Lippencott Co., Philadelphia, pp. 1048–1060, 1987). One use is to assess deficiencies in the extrinsic pathway of coagulation (factors VII, X, V, and prothrombin). A second use is to monitor patients undergoing long term oral anticoagulant therapy for disorders such as recurrent venous thrombosis and cancer (Hirsh, J., Seminars in Thrombosis and Hemostasis, 12:1–11, 1986). A third use is to evaluate liver dysfunction.

The therapeutic range of anticoagulant therapy is based on the avoidance of bleeding and thrombolic complications. When monitoring oral anticoagulant therapy, as well as for a variety of other conditions by the PT test, an elongation of prothrombin time by a factor of 2 is most desirable for long term therapy (O'Reilly, Hemostasis and Thrombosis, Basic Principles and Clinical Practice, Coleman, et al., eds., J. B. Lippencott Co., Philadelphia, pp. 1367–1372, 1987). This elongation factor is defined as the prothrombin ratio (PR) and is calculated by dividing the PT of a patient plasma by the PT of a pool of plasmas from normal individuals. A higher PR indicates a more sensitive PT reagent. The benefits of a more sensitive reagent for monitoring anticoagulation therapy is the use of lower doses of anticoagulant drug. These lower doses still provide adequate protection against thromboembolic disease while minimizing bleeding complications.

Several reagents for determining PTs are commercially available. These include Thromborel S (Curtis Matheson Scientific, Inc., Yorba Linda, Calif.) and Simplastin (Organon Teknika Corp., Charlotte, N.C.). These reagents yield very different PTs for the same patient plasma, with Thromborel S exhibiting a longer time than Simplastin. Lower doses of anticoagulant drug are therefore required to maintain extended PT times (high PR) when the PTs are monitored using Thromborel S instead of Simplastin. A need exists for an even more sensitive tissue factor based PT reagent to monitor anticoagulant therapy and other conditions. The present invention provides just such a sensitive reagent with its highly desirable PR.

SUMMARY OF THE INVENTION

The present invention relates to tissue factor reagents which comprise liposome compositions having tissue factor associated with the lipid bilayer wherein the lipid bilayer comprises a mixture of phospholipids and to methods for preparation of such compositions. The ratio of the lipid bilayer of the phospholipids in the liposomes provided, allows for maximum coagulant activity of the resulting tissue factor reagent and, thus, advantageous sensitivity of the reagent to the extrinsic coagulation factors being assessed.

Among other factors, the present invention is based on the surprising findings that the tissue factor reagent of this invention comprises liposomes having tissue factor associated with their lipid bilayer has been found to be an active procoagulant complex, a complex which is capable of efficient conversion of the proenzyme, factor VII, to the active coagulation protease, factor VIIa. This finding was surprising since neither tissue factor alone in solution nor the phospholipid mixture which makes up the liposomes' lipid bilayer alone is active as a prothrombin time reagent. I have also found that compositions of the present invention which further comprise glycine exhibit substantially improved performance in PT assays by rendering prothrombin times for normal human plasma equivalent to those of commercial controls designed to mimic human plasma.

Thus, according to one preferred aspect, the present invention is directed to tissue factor reagents which comprise liposome compositions useful for determining prothrombin times, said liposome compositions comprising tissue factor associated with the lipid bilayer of the liposomes (or phospholipid vesicles), preferably in a buffer which contains both a cryopreservative and glycine. In another aspect, it is directed to a method for preparing these compositions.

In a preferred aspect of the invention, the method of preparing the liposomes utilizes a detergent having a relatively high critical micelle concentration to solubilize highly purified phospholipids. An especially preferred detergent is the zwitterionic detergent, 3-[(3-cholamidopropyl)dimethylammonio]-1-propanesulfonate (CHAPS). Tissue factor, also solubilized in detergent, is added with a carrier protein and the detergent is then removed. The detergent may be conveniently removed by conventional methods, such as by dialysis, by resin treatment or by dilution into a detergent-free solution. Liposomes having tissue factor associated with and inserted in their lipid bilayer form spontaneously as the detergent concentration of the surrounding solution is lowered.

DEFINITIONS

"BHT" refers to butyrated hydroxytoluene.

"CHAPS" refers to 3-[(3-cholamidopropyl)-dimethylammonio]-1-propanesulfonate.

"MOPS" refers to 3-(N-morpholino)-propanesulfonic acid.

"OTG" refers to octyl beta-D-thioglucopyranoside.

"Phospholipid" refers to an organic molecule derived from either glycerol (most commonly) or sphingosine. Phospholipids derived from glycerol (or phosphoglycerides) comprise a glycerol backbone, two fatty acid chains esterified to the first and second carbons of the glycerol and phosphoric acid esterified to the third carbon. Optionally, an alcohol moiety is esterified to the phosphoric acid.

"PC" refers to phosphatidyl choline, an uncharged phosphoglyceride having an alcohol moiety derived from choline is esterified to the phosphoric acid.

"PE" refers to phosphatidyl ethanolamine, a positively charged phosphoglyceride, having an alcohol moiety derived from ethanolamine is esterified to the phosphoric acid.

"PG" refers to phosphatidyl glycerol, a negatively charged phosphoglyceride, having an alcohol moiety derived from glycerol is esterified to the phosphoric acid.

"PS" refers to phosphatidyl serine, a negatively charged phosphoglyceride, having an alcohol moiety derived from serine is esterified to the phosphoric acid.

"Prothrombin time" is abbreviated as PT and refers to the time interval between the addition of a thromboplastin or prothrombin time reagent and the appearance of a clot in platelet poor, citrated plasma.

"Prothrombin ratio" is abbreviated as PR and refers to the prothrombin time of an individual's plasma (either normal or abnormal) divided by the prothrombin time of pool of normal individual plasmas.

"rTF" refers to recombinant tissue factor.

"TBS" refers to 20 mM Tris (pH 7.5) containing 150 mM sodium chloride.

DETAILED DESCRIPTION OF THE INVENTION

1. Preferred Tissue Factor Reagent Compositions

Figure 1:
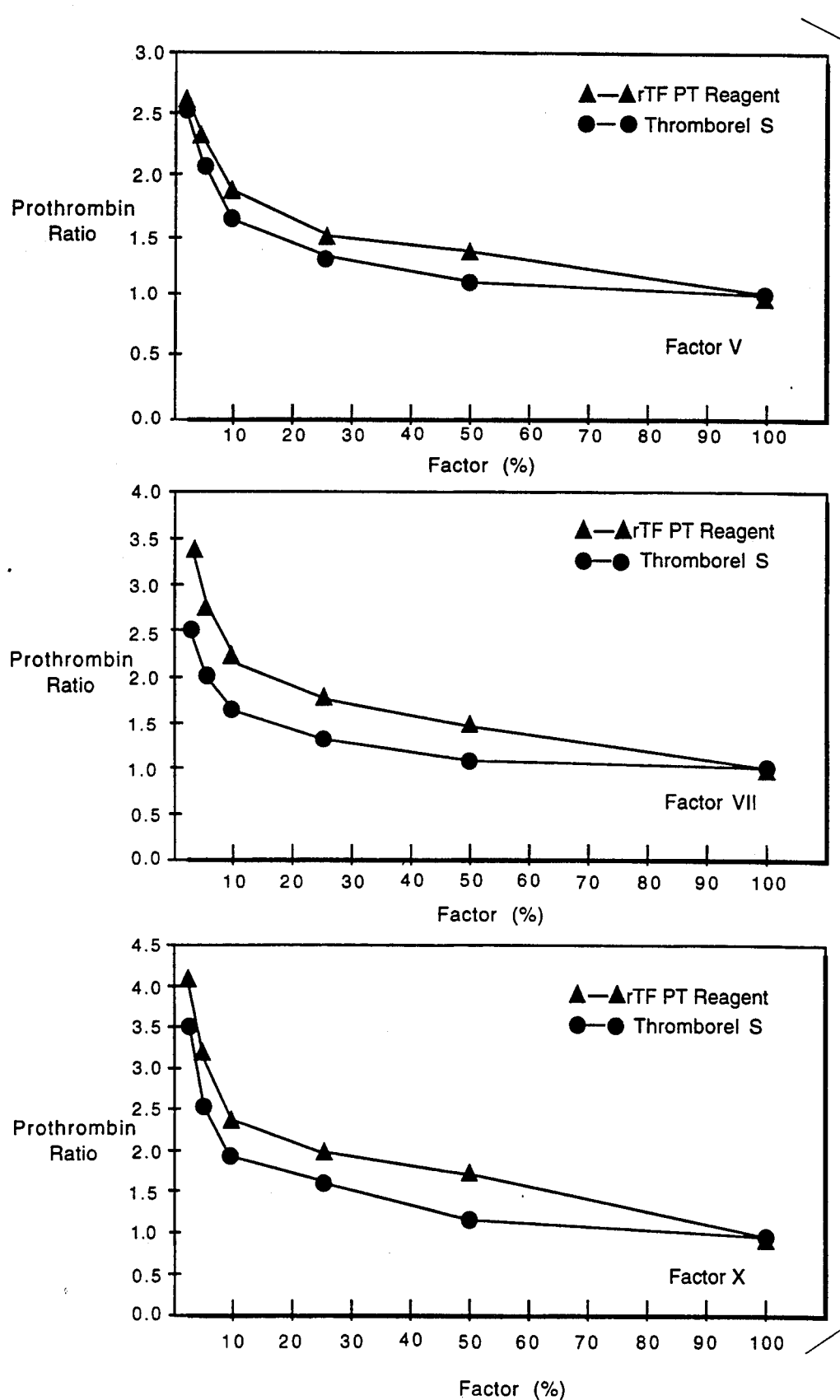
FIG. 1 shows the prothrombin ratios of PT reagents, rTF PT reagent and Thromborel S, as a function of percent factor activity.

The present invention provides tissue factor reagents which comprise liposomes having tissue factor associated with the lipid bilayer of the liposomes, such that the tissue factor is inserted through the lipid bilayer.

The lipid bilayer of the liposomes comprises phospholipids, preferably, phosphoglycerides.

Alternatively, according to another aspect of the present invention, tissue factor reagents are provided which comprise phospholipid micelle compositions which have tissue factor associated with phospholipid micelles such that the tissue factor is inserted into the micelle.

The tissue factor reagents of the present invention comprise about 0.1 µg to about 3 µg of natural or recombinant tissue factor per mg of phospholipid mixture. The ratio of tissue factor to phospholipid mixture may determine the sensitivity of the resulting tissue factor reagent. Thus, use of a ratio of about 1 to 2 µg tissue factor per mg phospholipid mixture may be suitable for a tissue factor reagent having a International Sensitivity Index ("ISI") of about 1.0. Use of a ratio of about 0.25 to about 0.5 µg tissue factor per mg phospholipid mixture may be suitable to prepare a tissue factor reagent having an ISI of about 1.6 to about 2.0. Preferred are tissue factor reagents that additionally comprise from about 0.5 to about 1.5% (w/v) glycine. Where it is desired to be able to lyophilize the tissue factor reagent to allow storage and later reconstitution, the reagent preferably includes a cryopreservative, preferably a carbohydrate preservative, most preferably trehalose.

A. Preferred Phospholipid Mixtures

Suitable phospholipids for use in the liposome compositions of the present invention include those which contain fatty acids having twelve to twenty carbon atoms; said fatty acids may be either saturated or unsaturated. Preferred phospholipids for use according to the present invention include phosphatidylcholine (PC), phosphatidylethanolamine (PE), phosphatidylglycerol (PG) and phosphatidylserine (PS). These phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain or spinal chord. These phospholipids may come from synthetic sources as well.

Phospholipid (PL) mixtures having a varied ratio of individual PLs may be used. Suitable PL mixtures comprise (a) from about 20 to about 95 mole percent PC; (b) from about 2.5 to about 50 mole percent PE; (c) from about 2.5 to about 50 mole percent PS; and (d) from about 0 to about 40 mole percent PG. Preferred are PL mixtures comprising from about 5 to 15 mole percent PE, from about 3 to about 20 mole percent PS, from about 10 to about 25 mole percent PG; and the remainder PC, preferably from about 50 to about 90 mole percent PC. Especially preferred are PL mixtures comprising from about 8 to about 12 mole percent PE, from about 3 to about 10 mole percent PS, from about 14 to about 20 mole percent PG and from about 58 to about 75 mole percent PC.

Although the phospholipids may be used in varied ratios, we have found that mixtures of phospholipids having certain amounts of individual phospholipids result in tissue factor reagents having advantageous activity and stability of activity. Although a wide range of ratios of individual phospholipids may be used, we have found that for advantageous activity and stability of the resulting tissue factor reagent a certain level of PS must be present in the total phospholipid composition. The amount of PS that is preferably present to some extent is determined by the remaining components of the PL mixture and their relative amounts as part of the total PL mixture. For example, use of high amounts of PG, another negatively charged phospholipid, (on the order of about 10% or more) allow use of lower levels of PS, on the order of about 3%. However, if a PL mixture low in PS is used, it is advantageous to include at least about 5% PE preferably at least about 10%.

The phospholipids are conveniently combined in the appropriate ratios to provide the PL mixture for use in preparing the tissue factor reagents of the present invention. In one preferred embodiment, the PL mixture may comprise PC, PG, PE and PS in the mole ratio of 67:16:10:7, respectively. In another preferred embodiment, the PL mixture may comprise PC, PG, PE and PS in the mole ratio of 7.5:0:1:1, respectively.

B. Tissue Factor

Either natural tissue factor or recombinant tissue factor may be used in the tissue factor reagents of the present invention. Natural or recombinant tissue factor from various species, may be used.

Natural tissue factor may be isolated by conventional methods. See, e.g., Broze, Jr., G. J., et al., *J. Biol. Chem*, 260(20):10917–10920 (1985); and Morrissey, J. H., et al., *Thrombosis Research* 50:481–493 (1988).

Recombinant tissue factor may prepared by recombinant technology using methods and expression systems known to the art. See, e.g., Morrissey, J. H., et al., *Cell* 50:129–135 (1987); Summers, M. D., "A Manual of Methods for Baculovirus Vectors and Insect Cell Culture Procedures," Texas Agricultural Experiment Station, Bulletin 1555 (1987).

Tissue factor may be purified by immuno affinity chromatography or other chromatographic methods designed to separate a specific protein from other protein contaminants.

C. Preferred Cryopreservatives

Cryopreservation relates to preserving the integrity of delicate substances when liquids containing them are frozen and dehydrated. The use of a carbohydrate as a cryopreservative of liposome integrity upon freezing and subsequent lyophilization has been reported. Racker, E., Membrane Biol., 10:221–235 (1972); Sreter, F. et al., Biochim. Biophys. Acta., 203:254–257 (1970); Crowe et al., Biochem. J., 242:1–10 (1987); Crowe et al., Biochim. Biophys. Acta., 987:367–384 (1988).

Where the tissue factor reagent will be lyophilized, prior to storage for later use, it is preferred to include a carbohydrate or carbohydrates as cryopreservative(s) to protect the integrity of liposomes in the resulting liposome composition during lyophilization and subsequent rehydration. Suitable carbohydrate cryopreservatives include trehalose, maltose, lactose, glucose and mannitol. According to a preferred aspect of the present invention, trehalose is included in aqueous buffer solution used in the preparation of the tissue factor reagents of the present invention (prior to lyophilization), preferably at a concentration in the range of about 50 mM to about 250 mM.

D. Glycine

According to a particularly preferred aspect of the present invention, glycine is included as an additional component of these tissue factor reagents. Inclusion of glycine in these tissue factor reagents results in reagents which exhibit substantially improved performance in PT assays giving prothrombin times for normal human plasma that are substantially equivalent to those of commercial controls designed to mimic human plasma. Thus, these preferred tissue factor reagents further comprise from about 0.5 percent to about 1.5 percent (w:v) glycine, more preferably from about 0.6 to about 1.2 percent glycine.

2. Preparation of Tissue Factor Reagents

The phospholipids, which may be obtained from the manufacturer in an organic solvent, are mixed together in the appropriate ratios to yield the specified composition. An antixiodant is then added to reduce alkyl chain peroxidation of the fatty acid portions of the phospholipids, and the organic solvent, if present, is removed by evaporation. One suitable antioxidant is butyrated hydroxy toluene. Preferably about 0.1% (by weight) of antioxidant is used.

The dried (evaporated) phospholipid mixture is then redissolved with an aqueous detergent solution. Suitable detergents include those which have a relatively high critical micelle concentration (CMC). Womack et al., Biochim. Biophys. Acta, 733:210 (1983). Such detergents include detergents having a CMC of greater than approximately 2 mM. Preferred are those detergents having a CMC of between approximately 2 to 25 mM. Such preferred detergents include 3-[(3-cholamidopropyl)-dimethylammonio]-1-propanesulfonate (CHAPS) and alkylglucopyranosides such as octyl beta-D-glucopyranoside, octyl beta-D-thioglucopyranoside and the like. Optionally, the detergent solution may include other components. These components may include buffer salts such as HEPES, Tris, phosphate, and the like; various other salts such as NaCl, KCl, and the like; a carbohydrate cryopreservative such as trehalose, maltose, glucose, and the like; and glycine. According to a preferred embodiment of the present invention, the detergent solution comprises 20 mM Tris, pH 7.5, 150 mM NaCl, (TBS) containing 100 mM CHAPS, 150 mM trehalose and 0.8% glycine. According to this preferred embodiment, the phospholipids are redissolved in this solution to give a final concentration of about 20 mg/ml.

Tissue factor and carrier protein are combined with the redissolved phospholipids and the volume of the resulting mixture is adjusted with a buffer as described above, preferably containing cryopreservative (most preferably trehalose) and glycine but no detergent. As noted above, the tissue factor used in the preparation of the tissue factor reagents of the present invention may be from either a natural or recombinant source. According to one preferred embodiment of the present invention, recombinant tissue factor (rTF) is used. Tissue factor is added followed by carrier protein, such as bovine gamma globulin, and sufficient buffer is added to adjust the final concentrations of tissue factor to 10 µg/ml, bovine gamma globulin to 1 mg/ml, phospholipid to 4 mg/ml and detergent to 20 mM. Suitable buffers include TBS containing 150 mM trehalose and 0.8% glycine. The resulting clear, colorless solution requires no vortexing or sonicating to ensure co-solubilization.

The detergent in the phospholipid-tissue factor mixture can be removed by a number of methods resulting in a stable liposome composition having tissue factor associated with and inserted through the lipid bilayer. Suitable methods of removal of detergent include dialysis, tangential flow diafiltration, cross flow hollow fiber filtration, treatment with hydrophobic chromatography resin, and simple dilution.

One preferred method of detergent removal from the phospholipid-tissue factor mixture utilizes dialysis for at least 30 hours at room temperature in dialysis membrane tubing against a buffer such as TBS containing 150 mM trehalose, 0.8% glycine and 0.05% NaN$_3$ to remove the detergent. Another preferred method of detergent removal utilizes resin treatment. Suitable resins include hydrophobic chromatographic resins such as Amberlite XAD-2 (Rohm and Haas Co. in Philadelphia, Pa.) or Bio-Beads SM-2 (BioRad in Richmond, Calif.). The resins may be used to remove the detergent, either by direct contact with the phospholipid-tissue factor solution or separated from it by a dialysis membrane. The rate of removal of detergent from the phospholipid-tissue factor solution is proportional to the weight ratio of the detergent in solution and the chromatographic resin beads.

The liposome solution resulting from the detergent removal step is then made to 5 mM CdCl$_2$. According to one preferred aspect, the liposome solution which contains the fully active tissue factor is diluted to a concentration 50 mM Tris, pH 7.5, 75 mM trehalose, 0.8% glycine and 10 to 15 mM CaCl$_2$ before use. Alternatively, the diluted reagent may be lyophilized for long term preservation of its performance characteristics as a prothrombin time reagent and then later reconstituted by suspension in water before use.

Another preferred method of detergent removal avoids the use of either dialysis or resin treatment and yet provides for preparation of active TF reagent. According to this method, detergent solubilized phospholipids containing TF are diluted into a buffer without detergent to produce mixed micelles containing TF which remain capable of being fully activated by CdCl$_2$. According to this aspect of the invention, phospholipids are dissolved to 20 mg/ml in a buffer containing detergent, preferably an alkyl glucopyranoside. A suitable buffer-detergent solution comprises 20 mM HEPES (pH 6) containing 50 mM octyl beta-D-thioglucopyranoside (OTG) and 150 mM NaCl. Carrier protein, TF, and CdCl$_2$ are then added and the mixture diluted further with buffer without detergent, such as 20 mM HEPES (pH 6) containing 150 mM NaCl, to yield final concentrations of TF at 10 µg/ml, carrier protein (bovine gamma globulin) at 1 mg/ml, CdCl$_2$ at 5 mM, phospholipids at 4 mg/ml, and OTG at 10 mM. The reagent may be lyophilized for storage as described above, or diluted as described above before use.

According to another aspect of the present invention, this reagent may be prepared by following methods for the preparation of vesicles and detergent-phospholipid mixed micelles from phospholipids by methods based on mechanical means, by removal of organic solvents, by detergent removal, and by size transformation as has been described by Lichtenberg, D. and Barenholz, Y., Methods of Biochemical Analysis, 33:337–462 (1988), and the disclosures of which are incorporated herein by reference.

To assist in understanding the present invention, the following examples are included, which describes the results of a series of experiments. The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLES

Example 1

Preparation of Anti-rTF Affinity Gel

The monoclonal antibody directed against TF, TF8-5G9 (ATCC number HC 938), was obtained from Dr. T. S. Edgington and was made by the procedure of Morrissey, J. H. et al., Thrombosis Research, 52:247-261 (1988). U.S. Pat. No. 5,110,730, the disclosures of which are incorporated herein by reference. The TF8-5G9 ascites was purified to IgG by DEAE chromatography using the procedure as described in Harlow, E and Lane, D., *Antibodies: A Laboratory Manual*, pp 304–305, Cold Spring Harbor Laboratory (1988).

The immunoaffinity resin was prepared by covalent attachment of the purified antibody to Affigel 10 (Biorad Laboratories in Richmond, Calif.) by the procedure recommended by the manufacturer. Thus, 200 mg of DEAE-purified monoclonal antibody was dialyzed into 0.1M MOPS (pH 7.5) to give a 10 mg/mL solution. 20 mL of this antibody solution was then added to 20 mL of Affigel 10. The mixture was then allowed to incubate overnight at 2° to 8° C. and mixed in an end-over-end fashion. After 16 to 24 hours, twenty mL of 0.1M ethanolamine (pH 8) was added to combine with any unreacted groups and terminate the coupling reaction. The resin was drained and washed with 0.1M MOPS (pH 7.5) and the immunoaffinity resin was stored at 2°-8° C. A coupling efficiency of greater than 95% was observed.

EXAMPLE 2

Preparation of Recombinant Tissue Factor (rTF)

Recombinant tissue factor (rTF) was purified from cell lysates using the following method. Cells producing rTF were washed with TBS and resuspended to $2 \times 10^7$/ml in TBS containing 0.25% Triton X100, 10 μg/ml soybean trypsin inhibitor, and 1 mM EDTA. After mixing for 30 minutes at 4° C., the cellular debris was removed by centrifuging for 20 min at about 5000×g at 4° C.

The clarified lysate was diluted 2.5-fold with TBS to reduce the Triton concentration to 0.1% and then was passed through the immunoaffinity resin (made in Example 1) containing a covalently coupled monoclonal antibody directed against TF. The resin bed was washed with 2 to 3 bed volumes of TBS+0.1% Triton X100, 2 to 3 volumes 20 mM Tris, pH 7.5, 0.5M NaCl, 0.1% Triton X100, and finally with 2 to 3 bed volumes 0.5M NaCl, 0.1% Triton X100. The bound protein was eluted from the resin with 0.1M glycine, pH 2.5, 0.1% Triton X100. Fractions collected after the buffer was changed to glycine were neutralized immediately with an appropriate volume of 1M Tris, pH 8. rTF was found in those fractions immediately surrounding the point where the pH of the column effluent had changed.

The fractions containing rTF were pooled, dialyzed against 20 mM Tris, pH 8, 0.1% Triton X100, and then concentrated by binding the rTF to a small bed volume DEAE Trisacryl column (IBF Biotechniques in Columbia, Md.). The Triton X100 was replaced with CHAPS by washing the resin bed with at least 10 bed volumes of 20 mM Tris, pH 8 containing 10 mM CHAPS. The rTF was eluted with a single step of 0.5M NaCl in the 20 mM Tris, pH 8,10 mM CHAPS.

EXAMPLE 3

Preparation of Phospholipids

Phosphatidylcholine (PC), phosphatidylethanolamine (PE), phosphatidylserine (PS) and phosphatidylglycerol (PG) were obtained in chloroform solution from Avanti Polar Lipids in Alabaster, Ala., or Calbiochem Corporation in La Jolla, Calif., in sealed glass ampules and stored under $N_2$ at $-20°$ C. CHAPS, other detergents and bovine gamma globulin were obtained from Calbiochem. Tris base and glycine were purchased from BioRad Laboratories in Richmond, Calif. All other chemicals and biochemicals were acquired from Sigma in St. Louis, Mo.

Phospholipids were prepared for resolubilization in the following manner. PC, PE, PS, and PG were warmed to room temperature and combined in a suitable tube or flask at the specified mole ratios. The antioxidant, butyrated hydroxytoluene (BHT), was dissolved in chloroform and added to the mixture of phospholipids at a weight ratio of 0.1% (BHT:total phospholipids). Organic solvent was removed by evaporation under a stream of dry nitrogen or under reduced pressure in a rotary evaporator. Residual organic solvent was eliminated by pumping an additional 1 hour at room temperature with a vacuum pump at a pressure of 10 μm or less. The mixture of phospholipids was redissolved to 20 mg/ml in 20 mM Tris, pH 7.5, 150 mM NaCl (TBS) containing 100 mM CHAPS.

EXAMPLE 4

Preparation of rTF Prothrombin Time (rTF PT) Reagent by Dialysis

Phospholipids were combined at the specified mole ratios of PC, PE, PS, and PG, then resolubilized as described in Example 3. The resolubilized phospholipids were combined with immunoaffinity-purified rTF (from Example 2) and bovine gamma globulin. Additional TBS containing 150 mM trehalose was added to yield final concentrations of 4 mg/ml total phospholipid, 10 ug/ml rTF, 1 mg/ml bovine gamma globulin and 20 mM CHAPS. This clear and colorless solution was placed in a dialysis membrane tubing (Spectrapore®, Spectrum Medical Industries, molecular weight cutoff of 12,000 to 14,000) and dialyzed for at least 30 hours at room temperature against TBS containing 150 mM trehalose and 0.05% $NaN_3$. After dialysis the volume of the dialysate was determined and adjusted back to the original volume, if required, with dialysis buffer. $CdCl_2$ was added to a final concentration of 5 mM and the solution was incubated at 37° C. for 2 hours.

The solution was frozen on dry ice, then lyophilized using a cycle beginning at $-40°$ C. and ending at room temperature, over a 48 hour period. The liposomes were then reconstituted to a working concentration with 0.1M Tris, pH 7.5, 150 mM trehalose to yield a solution containing rTF at approximately 1 to 2 μg/ml, phospholipids at approximately 400 to 800 μg/ml, and bovine gamma globulin at 50 to 100 μg/ml.

The rTF PT reagents, as prepared above, were used to determine the prothrombin times of Thromboscreen control plasmas (Curtin Matheson Scientific in Yorba Linda, Calif.) and a normal human plasma pool. Thus, 100 μl of plasma and 100 μl of diluted liposomes were placed in the sample well of a coagulometer. The instrument added 100 μl of 20 mM $CaCl_2$ and automatically determined the prothrombin time. The results are presented in Table I below.

TABLE I

Prothrombin Times of PT Reagent Prepared by Dialysis Using Various Ratios of Phospholipids

| Ratio of Phospholipids (PC:PE.PS:PG)[a] | NHP[b] | Average PT times in second | | |
|---|---|---|---|---|
| | | Level I[c] | Level II | Level III |
| 1:1:1:0 | 13.5 | 13.8 | 25.9 | 49.0 |
| 1:1:0:0 | 60.0 | 164.2 | 108.1 | 246.1 |
| 1:0:1:0 | 12.6 | 14.7 | 30.4 | 52.7 |
| 3:1:1:0 | 13.4 | 19.5 | 53.4 | 69.9 |
| 3:1:0:0 | 77.5 | 229.4 | —[d] | 231.1 |
| 3:0:1:0 | 17.3 | 27.5 | 70.1 | 98.2 |
| 5:1:1:0 | 11.1 | 13.1 | 35.2 | 65.4 |
| 5:0:1:0 | 10.7 | 13.5 | 34.8 | 66.1 |
| 10:1:1:0 | 12.4 | 16.4 | 48.4 | 89.2 |
| 10:0:1:0 | 14.9 | 21.0 | 62.7 | 112.6 |
| 20:1:1:0 | 18.4 | 27.5 | 82.9 | 147.6 |
| 7.5:1:0.5:1 | 10.2 | 18.6 | 48.8 | 82.7 |
| 8.5:0:0.5:1 | 13.6 | 27.9 | 78.2 | 131.8 |
| 8:1:0.25:1 | 13.8 | 27.2 | 76.1 | 128.1 |
| 9:0:0.25:1 | 17.5 | 35.7 | 103.4 | 187.6 |
| 7:1:0.25:2 | 10.7 | 18.4 | 54.5 | 98.0 |
| 8:0:0.25:2 | 13.7 | 26.1 | 76.8 | 118.8 |
| 7:1:0.1:2 | 12.6 | 23.0 | 70.2 | 119.8 |

TABLE I-continued

Prothrombin Times of PT Reagent Prepared by
Dialysis Using Various Ratios of Phospholipids

| Ratio of Phospholipids (PC:PE:PS:PG)[a] | NHP[b] | Average PT times in second | | |
|---|---|---|---|---|
| | | Level I[c] | Level II | Level III |
| 8:0:0.1:2 | 17.4 | 34.1 | 108.2 | 193.7 |

[a]The ratio of phospholipids is expressed as the mole ratio of phosphatidylcholine to phosphatidylethanolamine to phosphatidylserine to phosphatidylglycerol, respectively.
[b]Normal human pool (NHP) is composed of plasma pooled from 10 normal individuals, divided into small aliquots and snap frozen.
[c]Level I, II and III are Thromboscreen control plasmas (Curtin Matheson Scientific, Yorba Linda, California) and are designed to simulate patients undergoing 3 different levels or intensities of oral anticoagulant therapy.
[d]This time was greater than 300 sec.

The data indicated that (1) a wide range of phospholipid mole ratios in the rTF PT reagent is acceptable for rTF mediated initiation of the clotting mechanism, (2) the reagent requires a phospholipid composition carrying a net negative charge such as PS or PG for rTF-induced clotting activity, and (3) the reagent requires PE and PG together when PS is substantially reduced in concentration.

The control plasmas used in Table I are designed to simulate plasmas from patients undergoing oral anticoagulant therapy. The prothrombin times obtained using them do not indicate a deficiency in any one coagulation factor but instead reflect a depression of the activities of several factors.

An example of how the rTF PT reagent responds to reduced levels of several factors involved in the extrinsic coagulation pathway (factors V, VII, X) is presented in FIG. 1. The prothrombin (PT) times were determined in the following manner. Normal human plasma pool was diluted 1:2, 1:4, 1:10, 1:20, and 1:40 with 0.15M NaCl to yield 50, 25, 10, 5 and 2.5% factor activity, respectively. Coagulation factor deficient plasma samples (Thromboscreen, Curtis Matheson Scientific, Inc.) were rehydrated as suggested by the manufacturers and were used undiluted. The rTF PT reagent used here was made with phospholipid ratio of 10:1:1 (PC:PE:PS, respectively) and contained 10 mM $CaCl_2$. Thromborel S (Berhing Diagnostics in Somerville, N.J.) was rehydrated and handled according to manufacturer's recommendation. One hundred μl diluted normal human plasma (NHP) and 100 μl coagulation factor deficient plasma were placed in a coagulometer sample well. The PT reagent (200 μ;) was added by the instrument and the PT was determined automatically. The prothrombin ratio (PR) was calculated by dividing the coagulation factor deficient PT by the PT obtained with undiluted NHP and was plotted against the per cent of factor supplied by the NHP.

The data in FIG. 1 show that use of the rTF PT reagent resulted in higher PRs with all of the plasma dilutions tested. A PT reagent that exhibits a higher PR than another PT reagent at the same normal plasma pool dilution is said to be the more sensitive reagent. Therefore, the rTF PT reagent is more sensitive than the Thromborel S to depletion of the specific coagulation factors tested.

EXAMPLE 5

Preparation of rTF Prothrombin Time (rTF PT) Reagent Without Dialysis

Phospholipids were prepared for resolubilization in the following manner. PC, PE, and PS were warmed to room temperature and combined in a suitable tube or flask at a mole ratio of 7.5:1:1 of PC, PE, and PS, respectively. The antioxidant, butyrated hydroxytoluene (BHT), was dissolved in chloroform and added to the mixture of phospholipids at a weight ratio of 0.1% (BHT:total phospholipids). Organic solvent was removed by evaporation under a stream of dry nitrogen or under reduced pressure in a rotary evaporator. Residual organic solvent was eliminated by pumping an additional 1 hour at room temperature with a vacuum pump at a pressure of 10 μm or less.

The mixture of phospholipids was redissolved in 50 mM octyl beta-D-thioglucopyranoside (OTG) in 20 mM HEPES (pH 6), 150 mM NaCl to a final concentration of 4 mg/ml. rTF from Example 2 and bovine gamma globulin were mixed with the resolubilized phospholipids. Enough 20 mM HEPES (pH 6), 150 mM NaCl was added to adjust the final concentrations to 10 μg/ml rTF, 1 mg/ml bovine gamma globulin, 4 mg/ml phospholipids, and 10 mM OTG. $CdCl_2$ was added to a final concentration of 5 mM to activate the rTF. The resulting mixed micelles comprised of rTF, OTG, and phospholipids were diluted with 20 mM HEPES, pH 6, 150 mM NaCl to yield a solution containing rTF at approximately 0.5 to 1 μg/ml, phospholipids at approximately 500 to 700 μg/ml, and bovine gamma globulin at 25 to 50 μg/ml to give rTF PT reagent.

This reagent in this example was used to determine the PT of Thromboscreen control plasmas and a normal human plasma pool. The plasma controls are manufactured to mimic plasma which contain different levels of activities of coagulation factors II, V, VII and X. Control I contains near normal activity levels, Control II contains intermediate levels, while Control III contains the lowest levels. It is expected that the PTs should be the shortest with Control I and longest with Control III. The results in Table II below illustrate that this is the case.

TABLE II

Prothrombin Times with Control Plasmas Using Corvas rTF PT Reagent Prepared without Dialysis[a]

| Plasma Sample | Average PT time in seconds |
|---|---|
| Normal human plasma pool | 12.5 |
| Thromboscreen Control Plasmas: | |
| Level I | 13.7 |
| Level II | 37.1 |
| Level III | 81.1 |

[a]The normal human plasma and Thromboscreen control plasmas are described in the footnote of Table I.

The sensitivity of this rTF PT reagent was also compared with other commercial prothrombin time (PT) reagents using plasmas from patients undergoing oral anticoagulant therapy. The commercial reagents were Thromborel S (Berhing Diagnostics in Somerville, N.J.) and Simplastin (Organon Teknika Corporation in Charlotte, N.C.). The plasma samples, which were drawn from normal individuals and patients undergoing oral anticoagulant therapy, were obtained frozen from a local hospital.

Figure 2:
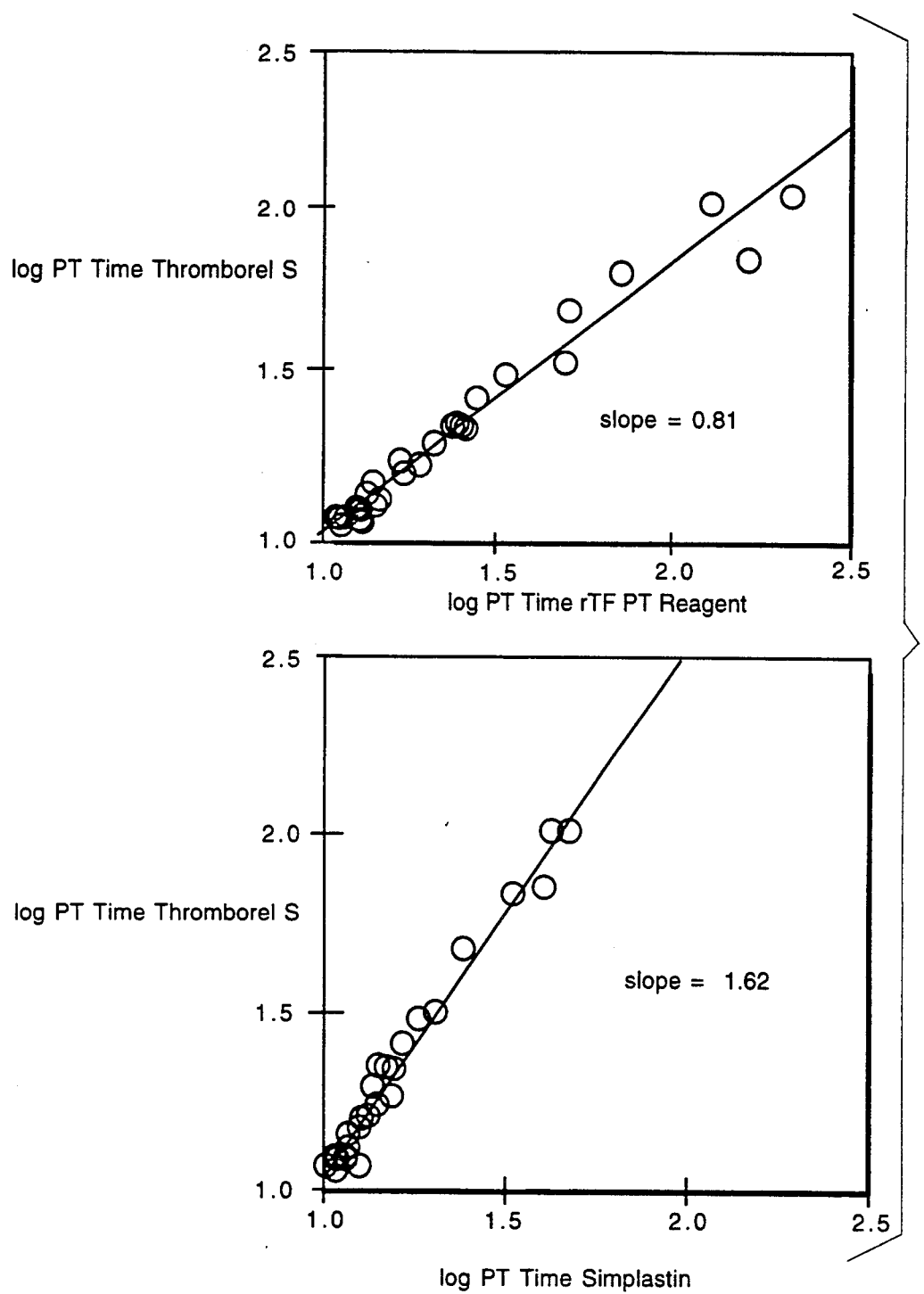
FIG. 2 shows the relative sensitivities of PT reagents to plasmas from patients undergoing oral anticoagulant therapy.

The prothrombin time for each plasma sample was determined using each of the three PT reagents. Thus, 100 μl of plasma and 100 μl of rTF PT reagent were placed in the sample well of a coagulometer. The instrument added 100 μl of 20 mM $CaCl_2$ and automatically determined the prothrombin time. With Thromborel S and Simplastin, 100 μl plasma were placed in the sample well and the instrument added 200 μl of PT reagent. The logarithm of the prothrombin time for each patient sample obtained using the rTF PT reagent and Simplastin was plotted against the same using Thromborel S. The data shown in FIG. 2 illustrate that for rTF PT reagent and Thromborel S, the slope is 0.81. A slope of 1.0 would indicate identical performance for the two PT reagents. Thus, the rTF PT reagent is approximately 20% more sensitive than Thromborel S. However, the slope of the line observed in the graph comparing Simplastin and Thromborel S is 1.62, indicating that Simplastin is much less sensitive than is Thromborel S. The data above confirm the conclusion drawn from Table II that the rTF PT reagent is sensitive to decreases in coagulation factor activities and that this sensitivity is seen in both actual and simulated patient plasmas.

EXAMPLE 6

Preparation of rTF Prothrombin Time Reagent by Diafiltration

Phospholipids were combined at mole ratio of 7.5:1:1 (PC:PE:PS), dried to remove organic solvent, then resolubilized as described in Example 3. The resolubilized phospholipids at 15 mg/ml in TBS containing 100 mM CHAPS were combined with immunoaffinity purified rTF (from Example 2) and bovine gamma globulin. Additional TBS containing 150 mM trehalose was added to yield final concentrations of 4 mg/ml phospholipid, 10 ug/ml rTF, 1 mg/ml bovine gamma globulin and 20 mM CHAPS.

The detergent (CHAPS) was removed by tangential flow diafiltration using, a Pyrostart or Ultrastart filter unit (Sartorius Corp., Bohemia, N.Y., molecular weight cutoff of 20,000) and TBS containing 150 mM trehalose as the dialysis buffer. Approximately 95 to 100% of the CHAPS can be removed by passing 10 volumes of dialysis buffer through the device. After diafiltration the volume of the dialysate was determined and adjusted back to the original volume (if required) with TBS containing 150 mM trehalose and 0.05% NaN$_3$. CdCl$_2$ was added to a final concentration of 5 mM and the solution was incubated at 37° C. for 2 hours.

The solution may be frozen on dry ice, then lyophilized using a cycle beginning at −40° C. and ending at room temperature, over a 48 hour period. The resulting reagent may be reconstituted to working concentration with the addition of 0.1M Tris, pH 7.5, 150 mM trehalose to yield a solution containing rTF at approximately 1 to 2 $\mu$g/ml, phospholipids at approximately 400 to 800 $\mu$g/ml, and bovine gamma globulin at 50 to 100 $\mu$g/ml. The reagent performance was similar that observed in Table II.

EXAMPLE 7

Preparation of rTF Prothrombin Time Reagent by Addition of XAD-2 Resin

Phospholipids were combined at mole ratio of 67:16:10:7 (PC:PG:PE:PS), dried to remove organic solvent, then resolubilized as described in Example 3. The resolubilized phospholipids at 15 mg/ml in TBS containing 100 mM CHAPS and 0.8% glycine were combined with immunoaffinity purified rTF (from Example 2) and bovine gamma globulin. Additional TBS containing 150 mM trehalose and 0.8% glycine was added to yield final concentrations of 3 mg/ml phospholipid, 4.5 $\mu$g/ml rTF, 1 mg/ml bovine gamma globulin and 20 mM CHAPS.

Hydrophobic chromatographic resins such as Amberlite XAD-2 (Rohm and Haas Co., Philadelphia, Pa.) or Bio-Beads SM-2 (BioRad, Richmond, Calif.) can also be used to remove the detergent (CHAPS), either in direct contact with the phospholipid solution or separated from it by a dialysis membrane. The rate of removal was proportional to the weight ratio of the detergent in solution and the chromatographic resin beads. Indeed, the rate of removal is proportional to both the amount of resin added and the rate of addition. The amount required to remove all of the detergent is calculated from the capacity of the resin (provided by the manufacturer) and the total mass of detergent to be removed. Moreover, 99.9% removal of the detergent may be achieved either in 1 hour or in 24 hours, at 30° C. depending upon the rate at which this amount of resin is added. CdCl$_2$ was added to a final concentration of 5 mM and the solution was incubated at 37° C. for 2 hours. The liposomes were then diluted to a working concentration with 50 mM Tris, pH 7.5, 75 mM trehalose, 15 mM CaCl$_2$, 0.8% glycine, 1% maltose, and 0.05% NaN$_3$ to yield a solution containing rTF at approximately 0.04 to 0.20 $\mu$g/ml, phospholipids at approximately 40 to 150 $\mu$g/ml, and bovine gamma globulin at 50 to 100 $\mu$g/ml.

The solution was frozen on dry ice, then lyophilized using a cycle beginning at −40° C. and ending at room temperature, over a 48 hour period. The lyophilized reagent was reconstituted with distilled water prior to use.

The performance of the rTF PT reagent was determined and the results are shown in Table III below. Thus, 100 $\mu$L of a normal human plasma pool or Ortho control plasmas were placed in a coagulometer sample well. The instrument added 200 $\mu$L of rTF PT reagent and determined the PT.

TABLE III

Prothrombin Times with Control Plasmas Using Corvas rTF PT Reagent Prepared By XAD-2 Treatments

| Plasma Sample | Average PT time in seconds |
| --- | --- |
| Normal human plasma pool | 12.1 |
| Ortho Control Plasmas: | |
| Level I | 11.8 |
| Level II | 35.7 |
| Level III | 63.1 |

$^a$Normal human pool (NHP) is composed of plasma pooled from 10 normal individuals, divided into small aliquots and snap frozen. Level I, II and III are Ortho Diagnostic Systems control plasmas (Raritan, New Jersey) and are designed to simulate patients undergoing 3 different levels or intensities of oral anticoagulant therapy.

The data show that the rTF PT reagent gives the performance desired of the present invention. First, the PTs for the different controls reflect the changes expected as these controls are designed to simulate the plasmas from patients undergoing various degrees of anti-coagulant therapy. Second, the PTs for the normal human plasma match those of the Level I control. The latter effect is attributed to the inclusion of glycine in the reagent. Compare data in Tables I and III.

What is claimed is:

1. A prothrombin time reagent containing purified natural or recombinant tissue factor which comprises a liposome composition comprising:
    (a) a phospholipid mixture comprising:
        (i) from about 20 to about 95 mole percent phosphatidylcholine,
        (ii) from about 2.5 to about 50 mole percent phosphatidylethanolamine, (iii) from about 2.5 to about 50 mole percent phosphatidylserine, and (iv) from about 0 to 40 mole percent phosphatidylglycerol; and (b) from about 0.1 μg to about 3 μg of tissue factor per mg phospholipid mixture.

2. A prothrombin time reagent according to claim 1 further comprising from about 0.5 percent to about 1.5 percent glycine.

3. A prothrombin time reagent according to claim 1 or 2 further comprising a carbohydrate cryopreservative selected from a group consisting of trehalose, maltose, lactose, glucose, and mannitol.

4. A prothrombin time reagent according to claim 3 wherein the carbohydrate cryopreservative comprises about 50 mM to 250 mM trehalose.

5. A prothrombin time reagent according to claim 4 wherein said phospholipid mixture comprises from about 5 to about 15 mole percent phosphatidylethanolamine; from about 5 to about 20 mole percent phosphatidylserine, from about 10 to 25 mole percent phosphatidylglycerol and the remainder phosphatidylcholine.

6. A prothrombin time reagent according to claim 4 wherein said phospholipid mixture comprises about 8 to about 12 mole percent phosphatidylethanolamine, from about 3 to about 10 mole percent phosphatidyl serine, from about 14 to about 20 mole percent phosphatidylglycerol, and from about 58 to about 75 mole percent phosphatidylcholine.

7. A prothrombin time reagent according to claim 1 or 2 wherein said phospholipid mixture comprises about 8 to about 12 mole percent phosphatidylethanolamine, from about 3 to about 10 mole percent phosphatidyl serine, from about 14 to about 20 mole percent phosphatidylglycerol, and from about 58 to about 75 mole percent phosphatidylcholine.

8. A prothrombin time reagent according to claim 7 wherein said tissue factor is recombinant tissue factor.

9. A prothrombin time reagent according to claim 4, comprising from about 0.6 to about 1.2 percent (w/v) glycine.

* * * * *